US011478323B2

(12) United States Patent
Geiger

(10) Patent No.: US 11,478,323 B2
(45) Date of Patent: *Oct. 25, 2022

(54) MEDICAL TRAY ASSEMBLY

(71) Applicant: Chris Geiger, Castle Pines North, CO (US)

(72) Inventor: Chris Geiger, Castle Pines North, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 17/208,533

(22) Filed: Mar. 22, 2021

(65) Prior Publication Data
US 2022/0031418 A1 Feb. 3, 2022

Related U.S. Application Data

(63) Continuation of application No. 16/511,775, filed on Jul. 15, 2019, now Pat. No. 10,952,805, which is a continuation of application No. 14/702,386, filed on May 1, 2015, now Pat. No. 10,350,020.

(51) Int. Cl.
*A61B 50/33* (2016.01)
*F16M 13/02* (2006.01)
*A61B 90/50* (2016.01)
*A61B 50/20* (2016.01)
*F16M 11/20* (2006.01)
*F16M 11/14* (2006.01)

(52) U.S. Cl.
CPC ............. *A61B 50/33* (2016.02); *A61B 50/20* (2016.02); *A61B 90/50* (2016.02); *F16M 11/14* (2013.01); *F16M 11/2092* (2013.01); *F16M 13/022* (2013.01); *F16M 2200/028* (2013.01)

(58) Field of Classification Search
CPC ......... A61B 50/33; A61B 50/20; A61B 90/50; F16M 11/14; F16M 11/2095; F16M 13/022; F16M 2200/028; A47B 17/065; A47B 23/02; A47B 23/04; Y10T 403/32254; Y10T 403/32311; Y10T 403/32008; Y10T 403/32057; Y10T 403/32565
USPC ..... 108/4, 42, 47, 46, 5, 157.13, 25, 27, 28, 108/97, 98, 152; 211/85.13; 206/570, 206/363; 248/226.11, 231.85, 231.71, 248/176.1, 177.1, 178.1, 179.1, 180.1, 248/181.1, 181.2, 122.1, 121, 126, 288, 248/31, 276.1, 285, 286.1
See application file for complete search history.

(56) References Cited

U.S. PATENT DOCUMENTS

| 161,026 A | * | 3/1875 | Grummon |
| 490,541 A | | 1/1893 | Case |
| 1,342,388 A | | 6/1920 | Kuderer |
| 1,348,121 A | | 7/1920 | Kuderer |
| 1,460,697 A | | 7/1923 | Bendlin |
| 1,516,795 A | | 11/1924 | Schwarting |
| 1,525,114 A | | 2/1925 | Yoscary |

(Continued)

FOREIGN PATENT DOCUMENTS

| CH | 625866 | * 10/1981 |
| EP | 0 903 114 | 3/1999 |

(Continued)

*Primary Examiner* — Janet M Wilkens

(57) ABSTRACT

A staging tray has a bracket with a hook and a bumper. The hook and bumper are configured to be removably engaged with a lipped tray. A pivot mechanism pivotably connects the bracket to the staging tray. The pivot mechanism is selectively positionable into a plurality of positions.

16 Claims, 8 Drawing Sheets

(56) References Cited

U.S. PATENT DOCUMENTS

| | | | |
|---|---|---|---|
| 1,583,161 | A | 5/1926 | Malott |
| 1,658,891 | A | 2/1928 | Gauck |
| 1,733,487 | A | 10/1929 | Hackley |
| 1,974,213 | A | 9/1934 | Gilbert |
| 2,069,890 | A | 2/1937 | MacDuff |
| 2,148,307 | A | 2/1939 | Scott |
| 2,328,135 | A * | 8/1943 | Gack .................... A47B 27/02 403/71 |
| D139,569 | S | 11/1944 | O'Brien |
| 2,433,594 | A | 12/1947 | Calo |
| 2,616,647 | A | 11/1952 | Murchison |
| 2,702,649 | A | 2/1955 | Neilson |
| 2,717,505 | A | 9/1955 | Andersson |
| 3,067,016 | A | 12/1962 | Rozycki |
| 3,095,057 | A | 6/1963 | Kraeling |
| 3,095,835 | A | 7/1963 | Smith |
| 3,301,406 | A | 1/1967 | Scott |
| 3,341,268 | A | 9/1967 | Bickford |
| 3,366,230 | A | 1/1968 | Loran |
| 3,424,419 | A | 1/1969 | Siegel |
| 3,542,019 | A | 11/1970 | Gittins |
| 3,662,982 | A | 5/1972 | Antonius |
| 3,696,920 | A | 10/1972 | Lahay |
| 3,738,405 | A | 6/1973 | Ericson |
| 3,770,119 | A | 11/1973 | Hultberg et al. |
| 3,819,039 | A | 6/1974 | Erickson |
| 3,863,873 | A | 2/1975 | Cushing |
| 3,871,137 | A | 3/1975 | Grammatico |
| 3,888,353 | A | 6/1975 | Leifheit |
| 3,949,880 | A | 4/1976 | Fortunato |
| 4,011,951 | A | 3/1977 | Boyer |
| 4,024,590 | A | 5/1977 | Wendt |
| 4,042,109 | A | 8/1977 | Barcan |
| 4,163,372 | A | 8/1979 | Frye et al. |
| 4,229,420 | A | 10/1980 | Smith et al. |
| 4,342,391 | A | 8/1982 | Schainholz |
| 4,365,709 | A | 12/1982 | Lester |
| 4,512,466 | A | 4/1985 | Delang |
| 4,595,102 | A | 6/1986 | Cianci et al. |
| 4,596,245 | A | 6/1986 | Morris |
| D286,117 | S | 10/1986 | Wellington |
| 4,641,749 | A | 2/1987 | Link et al. |
| 4,730,725 | A | 3/1988 | Marshall, Sr. et al. |
| 4,793,483 | A | 12/1988 | Holmes |
| 4,854,456 | A | 8/1989 | Lee |
| 4,865,821 | A | 9/1989 | Langdon |
| 4,923,202 | A | 5/1990 | Breveglieri et al. |
| 4,988,062 | A | 1/1991 | London |
| 5,000,407 | A | 3/1991 | Juji et al. |
| D317,982 | S | 7/1991 | Morales |
| 5,046,624 | A | 9/1991 | Murphy et al. |
| 5,145,655 | A | 9/1992 | Darlak |
| 5,161,766 | A * | 11/1992 | Arima .................... A47B 23/02 248/444.1 |
| 5,170,804 | A | 12/1992 | Glassman |
| 5,201,430 | A | 4/1993 | Artzer |
| D337,830 | S | 7/1993 | Coyne et al. |
| 5,275,482 | A | 1/1994 | Grant |
| 5,301,807 | A | 4/1994 | Donahue |
| 5,339,955 | A | 8/1994 | Horan et al. |
| 5,352,218 | A | 10/1994 | Buckley et al. |
| 5,381,896 | A | 1/1995 | Simons |
| D355,552 | S | 2/1995 | Whited et al. |
| 5,411,036 | A | 5/1995 | Wilkes |
| 5,435,322 | A | 7/1995 | Marshall |
| 5,449,069 | A | 9/1995 | Pijanowski et al. |
| D365,481 | S | 12/1995 | McKeon |
| 5,511,674 | A * | 4/1996 | Boyd .................... A47B 23/04 206/363 |
| 5,520,689 | A | 5/1996 | Schläpfer et al. |
| 5,533,618 | A | 7/1996 | Pickets, Jr. |
| 5,542,533 | A | 8/1996 | Vargas, III |
| D376,943 | S | 12/1996 | Czyszon |
| 5,660,451 | A | 8/1997 | Glynn |
| 5,664,691 | A | 9/1997 | Boivin-Paradis |
| 5,690,403 | A | 11/1997 | Ellison et al. |
| 5,722,624 | A * | 3/1998 | Watt .................... A47B 21/0314 248/205.1 |
| 5,725,111 | A | 3/1998 | Choi |
| 5,779,053 | A | 7/1998 | Partika et al. |
| 5,792,125 | A | 8/1998 | Webb |
| 5,848,693 | A * | 12/1998 | Davis .................... A61B 50/33 206/370 |
| 5,871,015 | A | 2/1999 | Lofgren et al. |
| 5,944,014 | A | 8/1999 | Webb |
| 5,992,647 | A | 11/1999 | Malik |
| 6,019,102 | A | 2/2000 | Becker |
| 6,048,503 | A | 4/2000 | Riley et al. |
| 6,065,596 | A | 5/2000 | Cavanagh |
| 6,095,057 | A | 8/2000 | Corban |
| 6,142,152 | A | 11/2000 | Gawarecki |
| 6,193,932 | B1 | 2/2001 | Wu et al. |
| 6,257,408 | B1 | 7/2001 | Odierno |
| 6,345,873 | B1 | 2/2002 | Kim |
| 6,364,262 | B1 | 4/2002 | Gibson et al. |
| 6,367,637 | B1 | 4/2002 | Davis et al. |
| 6,426,041 | B1 | 7/2002 | Smith |
| 6,471,167 | B1 | 10/2002 | Myers et al. |
| 6,540,312 | B1 | 4/2003 | Lane |
| 6,622,861 | B2 | 9/2003 | Kissling |
| 6,629,615 | B2 | 10/2003 | Kim |
| 6,705,474 | B1 | 3/2004 | Buczek |
| 6,802,431 | B2 | 10/2004 | Schinkel |
| 6,823,805 | B2 | 11/2004 | Becker |
| 6,874,505 | B1 | 4/2005 | Fenwick et al. |
| 6,915,912 | B2 | 7/2005 | Davis et al. |
| 6,969,498 | B1 | 11/2005 | Riley |
| 7,040,484 | B1 | 5/2006 | Homra et al. |
| 7,066,328 | B2 | 6/2006 | Pulsifer |
| 7,104,201 | B2 | 9/2006 | Comeaux et al. |
| 7,124,988 | B1 | 10/2006 | Duffy et al. |
| 7,293,654 | B1 | 11/2007 | Wilson, Jr. et al. |
| RE40,432 | E | 7/2008 | Cavanagh |
| 7,409,953 | B2 | 8/2008 | Griesbach, III |
| 7,441,655 | B1 | 10/2008 | Hoftman |
| 7,457,506 | B1 | 11/2008 | Osborne, II |
| 7,461,751 | B2 | 12/2008 | Lyons |
| 7,517,118 | B2 | 4/2009 | Lefebvre et al. |
| 7,563,265 | B1 | 7/2009 | Murphy |
| D608,015 | S | 1/2010 | Sandel |
| D608,456 | S | 1/2010 | Sandel |
| 7,665,606 | B2 | 2/2010 | Gaillard |
| 7,673,754 | B2 | 3/2010 | Wilson, Jr. et al. |
| 7,766,289 | B2 | 8/2010 | Newkirk et al. |
| 7,798,331 | B2 | 9/2010 | Hardin et al. |
| D632,796 | S | 2/2011 | Ross et al. |
| D632,797 | S | 2/2011 | Ross et al. |
| 7,959,014 | B2 | 6/2011 | Dredla, IV |
| 7,980,517 | B2 | 7/2011 | Zoland et al. |
| D643,535 | S | 8/2011 | Ross et al. |
| 8,020,829 | B1 * | 9/2011 | Tamayori .................... B62B 9/26 248/447.2 |
| 8,074,815 | B2 | 12/2011 | Gerstner |
| 8,083,059 | B1 | 12/2011 | Wessel, IV |
| D652,521 | S | 1/2012 | Ross et al. |
| D652,936 | S | 1/2012 | Ross et al. |
| 8,240,684 | B2 | 8/2012 | Ross et al. |
| 8,370,977 | B2 | 2/2013 | Newkirk et al. |
| 8,371,448 | B1 | 2/2013 | Reaux |
| 8,453,280 | B2 | 6/2013 | Martray |
| 8,453,977 | B2 | 6/2013 | Zoland et al. |
| 8,459,265 | B2 | 6/2013 | Young et al. |
| 8,505,748 | B2 | 8/2013 | Jones et al. |
| 8,517,233 | B2 | 8/2013 | Podda-Heubach |
| 8,555,892 | B2 | 10/2013 | Traub |
| 8,707,961 | B1 | 4/2014 | Kazravan |
| 8,727,141 | B2 | 5/2014 | Akalin |
| 8,753,059 | B2 | 6/2014 | Baker |
| 9,033,162 | B2 * | 5/2015 | Brotzman .................... A61B 50/15 211/85.13 |
| 9,060,913 | B2 * | 6/2015 | Hensler .................... A61G 7/0518 |
| 10,350,020 | B2 * | 7/2019 | Geiger .................... F16M 11/14 |
| 10,952,805 | B2 * | 3/2021 | Geiger .................... A61B 50/20 |
| 2001/0033890 | A1 | 10/2001 | Kissling |

(56) References Cited

U.S. PATENT DOCUMENTS

| | | |
|---|---|---|
| 2001/0035384 A1 | 11/2001 | Davis et al. |
| 2003/0024891 A1 | 2/2003 | Diamond |
| 2003/0196922 A1 | 10/2003 | Reaux |
| 2005/0040066 A1 | 2/2005 | Pulsifer |
| 2005/0052066 A1* | 3/2005 | Wright ............... A61F 5/3761 297/411.36 |
| 2005/0098460 A1 | 5/2005 | Smith et al. |
| 2006/0180058 A1 | 8/2006 | Monson |
| 2007/0131149 A1* | 6/2007 | Mayben ............. F16M 13/022 108/97 |
| 2008/0000910 A1* | 1/2008 | Gaillard ............... A61B 50/10 220/482 |
| 2008/0296454 A1 | 12/2008 | Carnevali |
| 2009/0050516 A1 | 2/2009 | Hardin et al. |
| 2010/0270442 A1 | 10/2010 | Zoland et al. |
| 2011/0073507 A1 | 3/2011 | Isaacson |
| 2011/0155599 A1 | 6/2011 | Yakel |
| 2011/0173749 A1 | 7/2011 | Martray |
| 2011/0226766 A1 | 9/2011 | Baker |
| 2011/0240577 A1 | 10/2011 | Jones et al. |
| 2011/0284012 A1 | 11/2011 | McCollough |
| 2012/0024864 A1 | 2/2012 | Champ |
| 2013/0105346 A1 | 5/2013 | Ramkhelawan et al. |
| 2013/0164103 A1 | 6/2013 | Baker |
| 2013/0200023 A1 | 8/2013 | Brotzman et al. |
| 2014/0021087 A1 | 1/2014 | Adler et al. |
| 2014/0069841 A1 | 3/2014 | Pizzato et al. |
| 2014/0138269 A1 | 5/2014 | Ghosh |
| 2014/0138270 A1 | 5/2014 | Ghosh |
| 2016/0000993 A1 | 1/2016 | Endyk |

FOREIGN PATENT DOCUMENTS

| | | |
|---|---|---|
| EP | 1 237 494 B1 | 10/2006 |
| EP | 1 237 494 B9 | 2/2007 |
| ES | 2 386 640 | 8/2012 |
| GB | 2 381 521 | 5/2003 |
| JP | 3640640 | 4/2005 |
| WO | 01/41665 | 6/2001 |
| WO | 2003/075779 | 9/2003 |
| WO | 2008/148007 | 12/2008 |
| WO | 2011/123565 | 10/2011 |
| WO | 2012/101305 | 8/2012 |

* cited by examiner

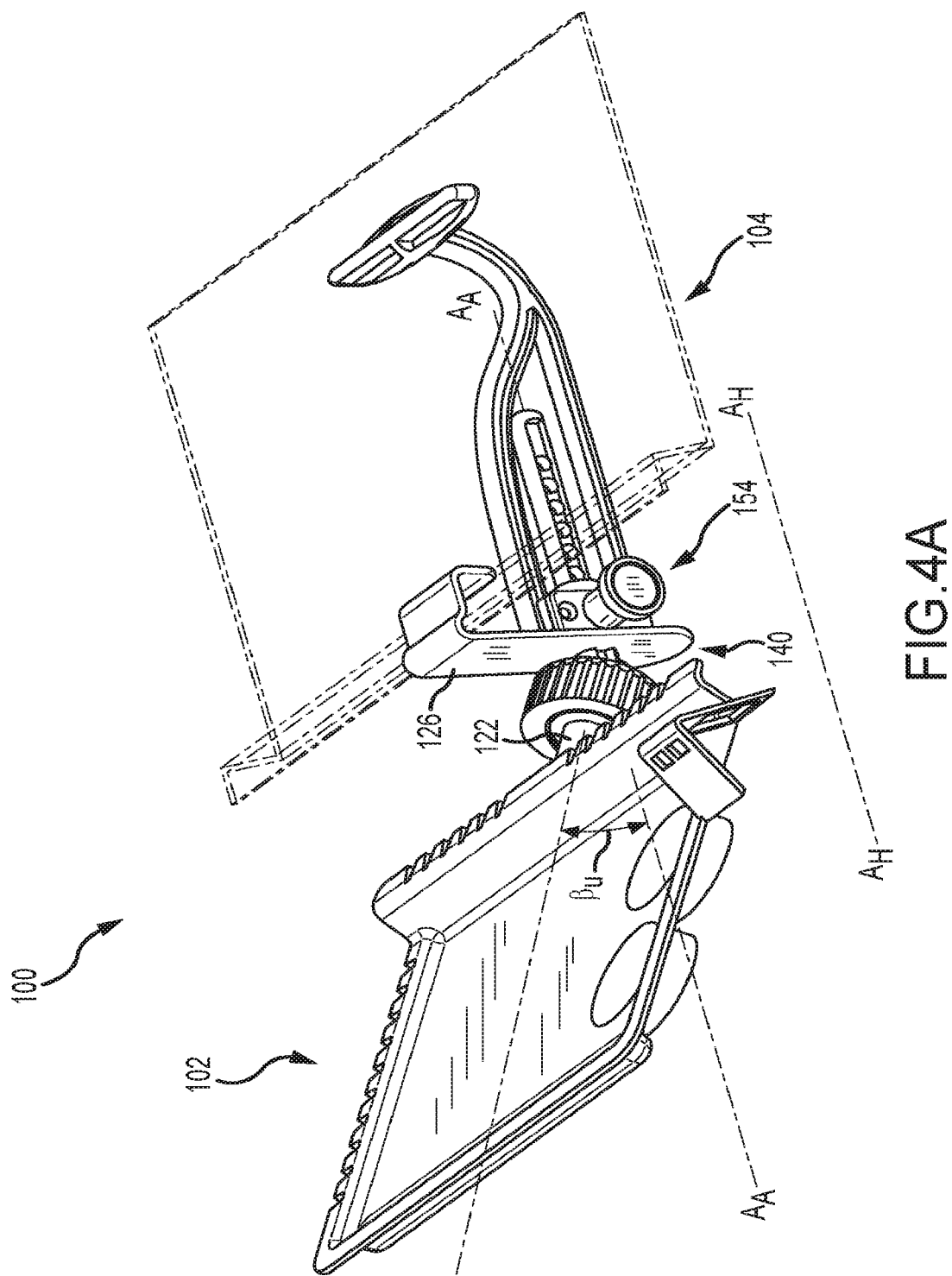

MEDICAL TRAY ASSEMBLY

CROSS-REFERENCE TO RELATED APPLICATIONS

This application is a continuation application and claims priority to U.S. patent application Ser. No. 16/511,775, filed Jul. 15, 2019, now issued U.S. Pat. No. 10,952,805, which is a continuation application and claims priority to U.S. patent application Ser. No. 14/702,386, filed May 1, 2015, now issued U.S. Pat. No. 10,350,020, which applications are hereby incorporated herein by reference in their entireties.

BACKGROUND

During a surgical procedure, e.g., neurosurgery, spinal surgery, otolaryngological surgery, facial plastic or reconstructive surgeries, and the like, a medical tray is generally disposed so as to be located over a patient's chest. The medical tray is available to a surgical technologist or scrub personnel for storage or placement of various surgical instruments, liquids, gauzes, etc. If the surgeon performing the operation requires one of the items located thereon, he or she typically asks the surgical technologist or scrub personnel for the item. This may be a distraction for the surgeon focused on their work. It is possible for the surgeon to access the medical tray directly and select the desired item, but the medical tray is often not positioned so it can be accessed by both the surgeon and the surgical technologist.

SUMMARY

In one aspect, the technology relates to an apparatus having: a staging tray; a bracket having a hook and a bumper, wherein the hook and the bumper are configured to be removably engaged with a lipped tray; and a pivot mechanism for pivotably connecting the bracket to the staging tray, wherein the pivot mechanism is selectively positionable into a plurality of positions. In an embodiment, the staging tray at least partially defines at least one of a trough and a receiver. In another embodiment, the staging tray has a raised edge, wherein at least a portion of the raised edge defines at least one of a plurality of slots, a plurality of teeth, and a plurality of crenellations. In yet another embodiment, the staging tray further includes a forceps receiver. In still another embodiment, the forceps receiver includes a receipt angle.

In another embodiment of the above aspect, the forceps receiver has a receipt angle. In an embodiment, the socket is fixedly connected to the tray. In another embodiment, the pivot mechanism has a locking element for selectively positioning the pivot mechanism into the plurality of positions. In yet another embodiment, the ball is fixedly engaged with an armature connected to the bracket. In still another embodiment, the armature is slidably engaged with the bracket. In another embodiment, the armature is selectively positionable in a plurality of positions.

In another aspect, the technology relates to an apparatus having: a bracket; and a staging tray movably engaged with the bracket, wherein the staging tray is configured to be positioned both angularly and linearly relative to the bracket. In an embodiment, an angular adjustment system includes: a ball and socket joint engaged with at least one of the bracket and the staging tray; and a rotatable lock for engaging at least one of the ball and the socket so as to selectively angularly position the staging tray relative to the bracket. In another embodiment, a linear adjustment system includes: an armature slidably engaged with at least one of the bracket and the staging tray; and a lock for engaging the armature so as to selectively linearly position the staging tray relative to the bracket. In yet another embodiment, at least one of the ball and the socket is fixed to the armature. In still another embodiment, the ball and socket joint is configured for movement along a single plane.

In another embodiment of the above aspect, the ball and socket joint is positionable in a first extreme position and a second extreme position approximately 90 degrees from the first extreme position. In an embodiment, the lock has at least one of a fixed pin, a retractable pin, a spring-loaded pin, and a clamp.

In another aspect, the technology relates to an apparatus having: a staging tray including: a staging surface, wherein the staging surface defines at least one receiver and at least partially defines a trough; and a raised perimeter substantially surrounding the staging surface, wherein at least a portion of the raised perimeter at least partially defines at least one cut-out. In an embodiment, the staging tray is configured to be positioned both angularly and linearly relative to the bracket.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

FIGS. 4A and 4B are front perspective views of the staging tray assembly of FIG. 1, depicting extreme linear and angular positions of the staging tray.

DETAILED DESCRIPTION

Figure 1:
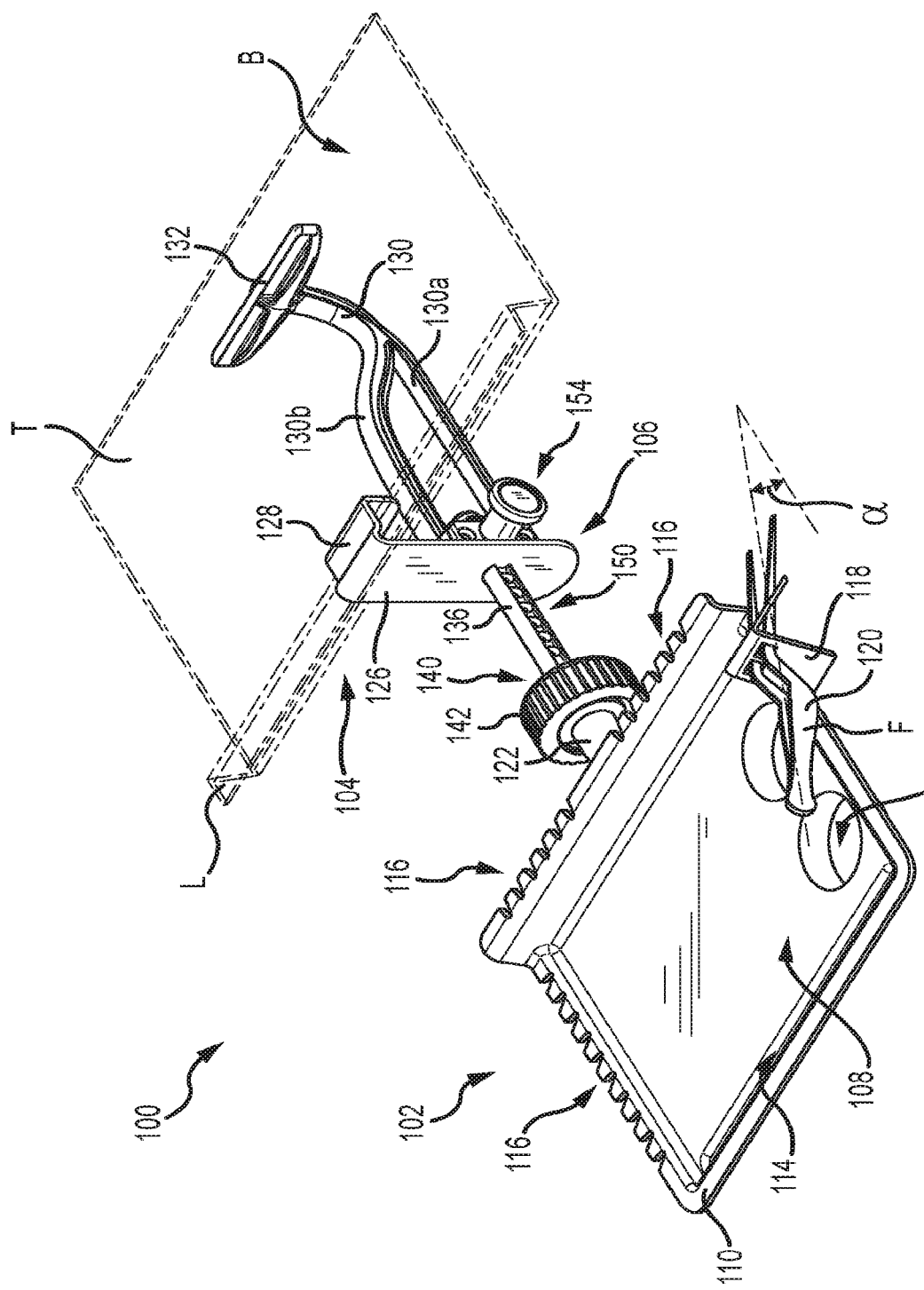
FIG. 1 is a front perspective view of a staging tray assembly in accordance with one embodiment of the technology, engaged with a medical tray.
Figure 2:
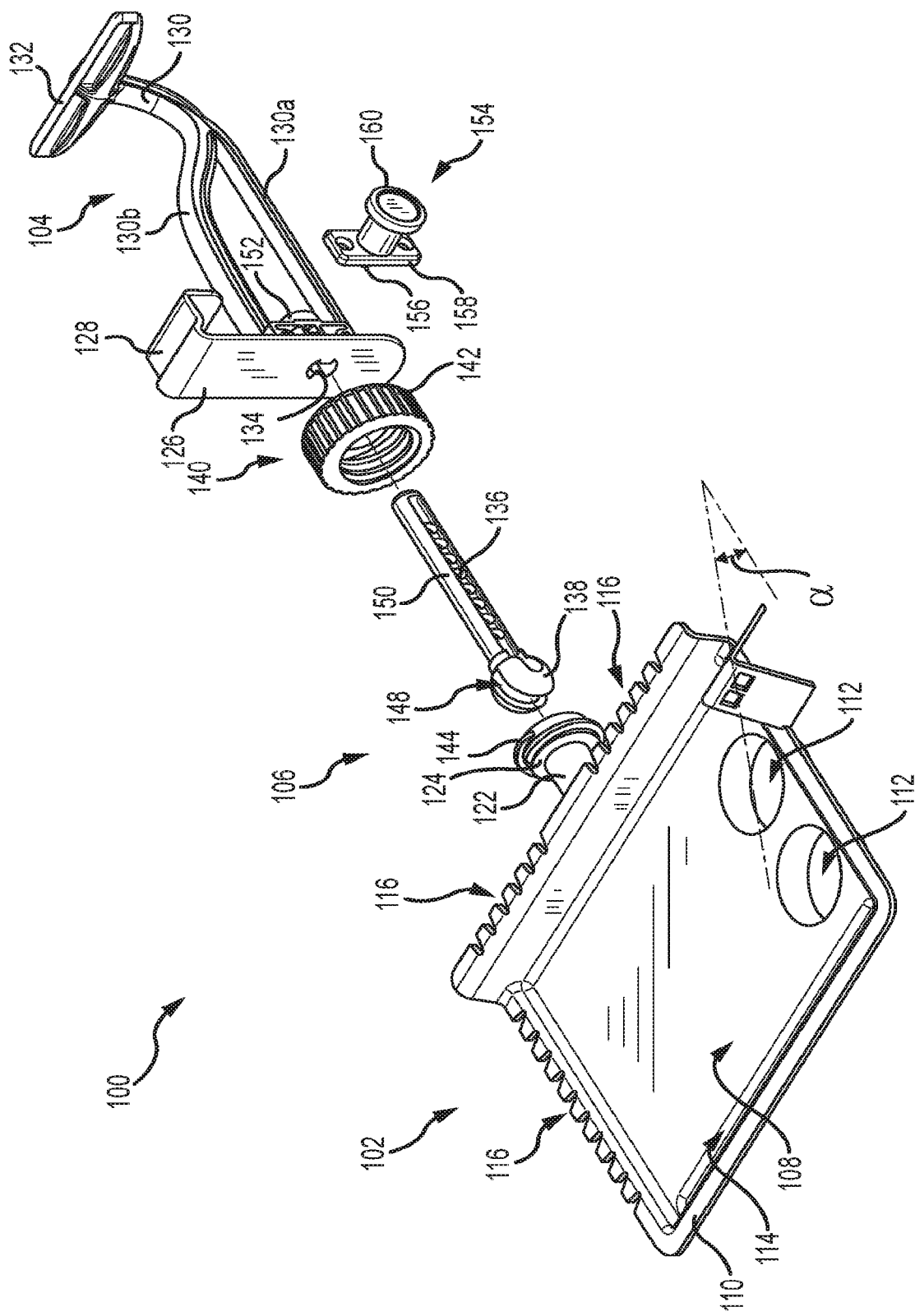
FIG. 2 is an exploded front perspective view of the staging tray assembly of FIG. 1.

FIGS. 1 and 2 are a front perspective and exploded front perspective views, respectively, of a staging tray assembly 100 engaged with a medical tray T. FIGS. 1 and 2 are described simultaneously. During a surgical procedure, e.g., neurosurgery, spinal surgery, otolaryngological surgery, facial plastic or reconstructive surgeries, and the like, the medical tray T is generally disposed so as to be located over a patient's chest, while the staging tray assembly 100 extends towards the patient's head. In such an arrangement, the medical tray T is available to a surgical technologist or other scrub personnel for storage or placement of various surgical instruments, liquids, gauzes, etc. Engagement of the staging tray assembly 100 to the medical tray T allows a surgeon to have readily available various items required for surgery. These items may be staged on the staging tray 102, and may include cotton patties, surgical gel foams, coagulants such as thombin and/or surgisil, stitches, clamps, forceps, etc. Thus, the surgeon is able to easily access these items without requesting such items from the surgical technologist. The medical tray T may be a mayo tray or other medical tray typically utilized in surgical suites. The medical tray T is depicted schematically herein and includes at least a base B and a lip L extending therefrom. The staging tray assembly 100 depicted herein can be used with any type of medical tray T having at least a base B. Although the staging tray assembly 100 is described herein generally in the context of a surgeon's use during brain surgery, the additional space and functionality available with the assembly 100 can be utilized by surgeons, surgical technologists, or other scrub personnel, in other operations or procedures, such as spinal surgery, otolaryngological surgery, facial plastic or reconstructive surgeries, and the like.

The staging tray assembly 100 includes the staging tray 102, a bracket 104, and an angular and linear adjustment system 106 disposed therebetween. The staging tray assembly 100 includes a base 108 substantially surrounded by a raised perimeter or edge 110. The base 108 at least partially defines one or more receivers 112 that can be utilized to hold cups of surgical liquids during surgery. These liquids can be thombin, surgisil, saline, or other liquids or fluids used for flushing, coagulation, etc. The base 108 also at least partially defines a trough 114, which is used to catch fluids that may weep off of the cotton patties or other items. The trough 114 prevents these fluids from dripping onto the surgical site or surgeon. The depicted trough 114 is positioned along one side of the edge 110, but may be formed proximate other or additional sides of the edge 110. The raised edges 110 can also be formed so as to provide hanging holders for sutures or stitches. For example, the edges 110 can at least partially define a plurality of slots, teeth, crenellations, or other shapes 116. Additionally, a forceps receiver 118 can be integrally formed or otherwise connected to the staging tray 102 to provide a convenient storage location for forceps F. Openings 120 on the forceps receiver 118 define a receipt angle α that is sufficiently steep so as to prevent the forceps F from sliding out therefrom, regardless of the angular position of the staging try 102. In the depicted embodiment, the forceps receiver 118 and the receivers 112 are disposed on a right side of the staging tray 102. Left-handed surgeons may wish to have either or both of these components disposed on the left side of the staging tray 102. A shaft 122 may be disposed and fixed at one end of the staging tray 102 and can include a portion of the angular and linear adjustment system 106. For example, in FIG. 1, the shaft 122 is fixedly connected to a socket 124, which is described in more detail below.

The bracket 104 is removably engageable with the tray T and includes an interface 126 that is integral with a hooked upper arm 128. The hooked upper arm 128 defines a plurality of curvatures so the bracket 104 can be utilized with medical trays T having varied lip L configurations. A lower arm 130 includes two portions 130a, 130b and extends from the interface 126. The lower arm 130 terminates at a bumper 132 that engages a bottom surface of the base B of the medical tray T during use. Although other bracket configurations may be utilized, it has been determined that brackets 104 having relatively wide hooks 128 and bumpers 132 prevent wobbling of the bracket 104. The interface 126 defines an opening 134 for receipt of a portion of the angular and linear adjustment system 106, in the depicted embodiment, an armature 136.

The angular and linear adjustment system 106 includes, in the depicted embodiment, a number of shared components and connects the bracket 104 to the staging tray 102. One portion of the system is a pivot mechanism that includes a socket 124 engaged with a ball 138. This ball and socket joint 140 enables pivotable connection between the shaft 122 and the armature 136. In certain embodiments, the ball and socket joint 140 may allow for multiple degrees of freedom, such that the maximum angular positions define a cone having an apex substantially centered on the ball 138. A limited-movement ball and socket joint 140 is described in FIG. 3, below. A locking element 142, in the form of a locking collar or wheel, engages one or more threads 144 on an outer portion of the socket 124. When rotated in a first direction, the locking element 142 can allow for pivoting movement of the staging tray 102 relative to the bracket 104, which remains fixed in position. A counter-rotation of the locking element 142 locks the position of the staging tray 102 in place. The armature 136 is connected to the ball 138 defines a plurality of openings 150 and is slidably received in the opening 134 in the interface 126. A base 152 is disposed proximate the opening 134 and provides a mounting element for another portion of the angular and linear adjustment system 106, a linear locking element 154. The linear locking element 154 includes an engagement element or pin 156 configured to engage the openings 150 in the armature 136. A plate 158 is utilized to mount the locking element 154 to the base 152 and a pull 160 enables a user to withdraw the pin 156 from one of the openings 150, so as to adjust a linear position of the staging tray 102 relative to the bracket 104. The pin 156 can be fixed, retractable, or spring-loaded, or a clamp may be used. Angular and linear adjustment systems having different components than those depicted in FIGS. 1 and 2 are also contemplated and described herein.

Figure 3:
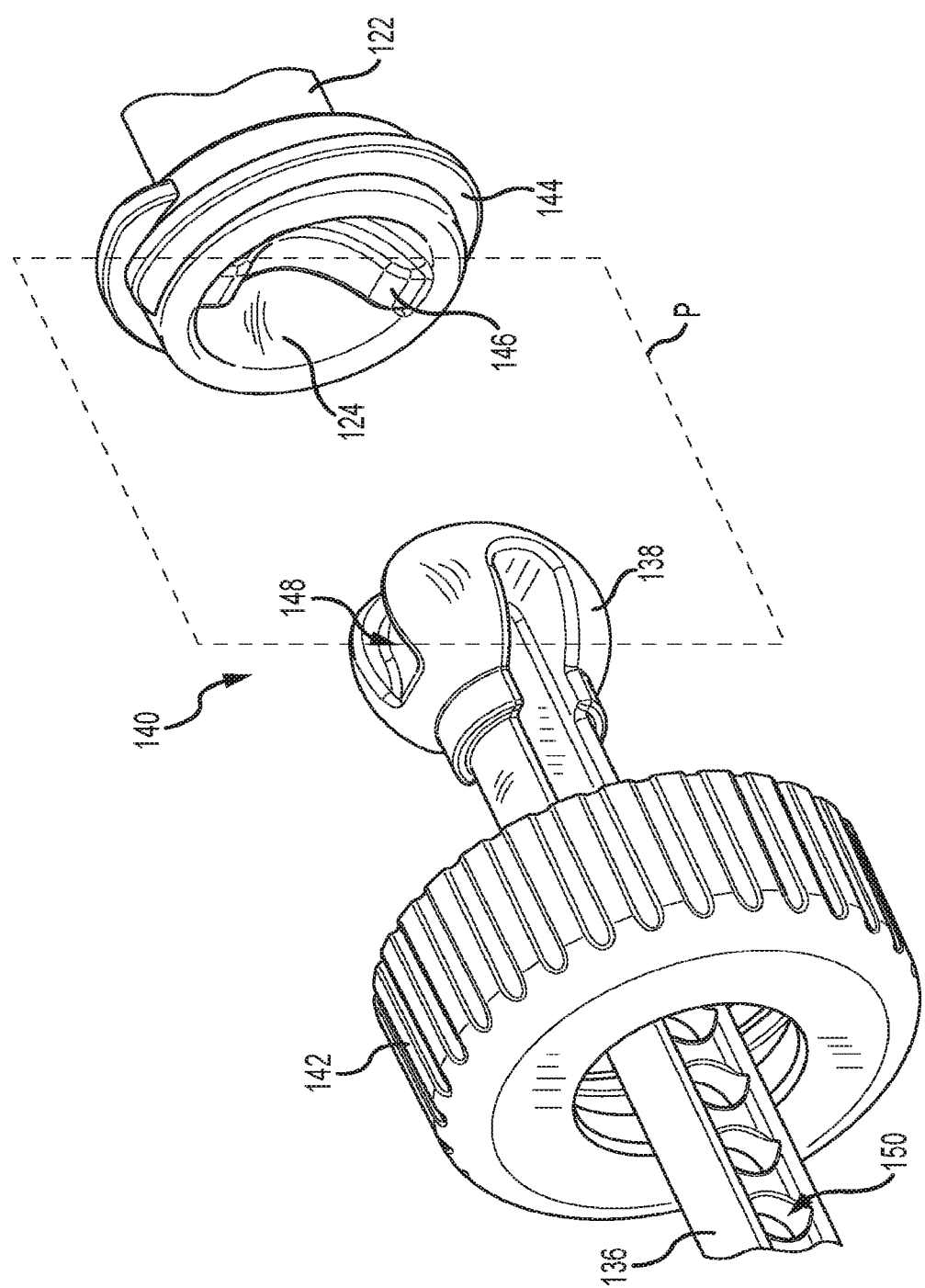
FIG. 3 is a partial exploded rear perspective view of an angular adjustment system.

FIG. 3 is a partial exploded rear perspective view of the angular adjustment system, specifically the ball and socket joint 140 of FIG. 1. Certain of the elements used therein are described above in FIGS. 1 and 2 and are therefore not necessarily described further. Here, the shaft 122 is depicted without the staging tray 102, which is not shown for clarity. In the depicted embodiment, a limited-movement ball and socket joint 140 is depicted. The socket 124 includes a projection or spine 146 disposed on an inner surface thereof. The spine 146 engages a slot 148 defined by the ball 138, thus limiting the movement of the ball and socket joint 140 to along a single plane P substantially parallel to both the spine 146 and the slot 148. Such an embodiment displays more limited positioning than a ball and socket joint that does not utilize the engaging projection 146 and slot 148. In fact, the engaging projection 146 and slot 148 allow only for two-dimensional pivoting movement, akin to that of a hinge. However, such a limited-movement ball and socket joint 140 may be desirable, as it prevents inadvertent tipping of the staging tray 102 to the sides during positioning thereof.

Figure 4B:
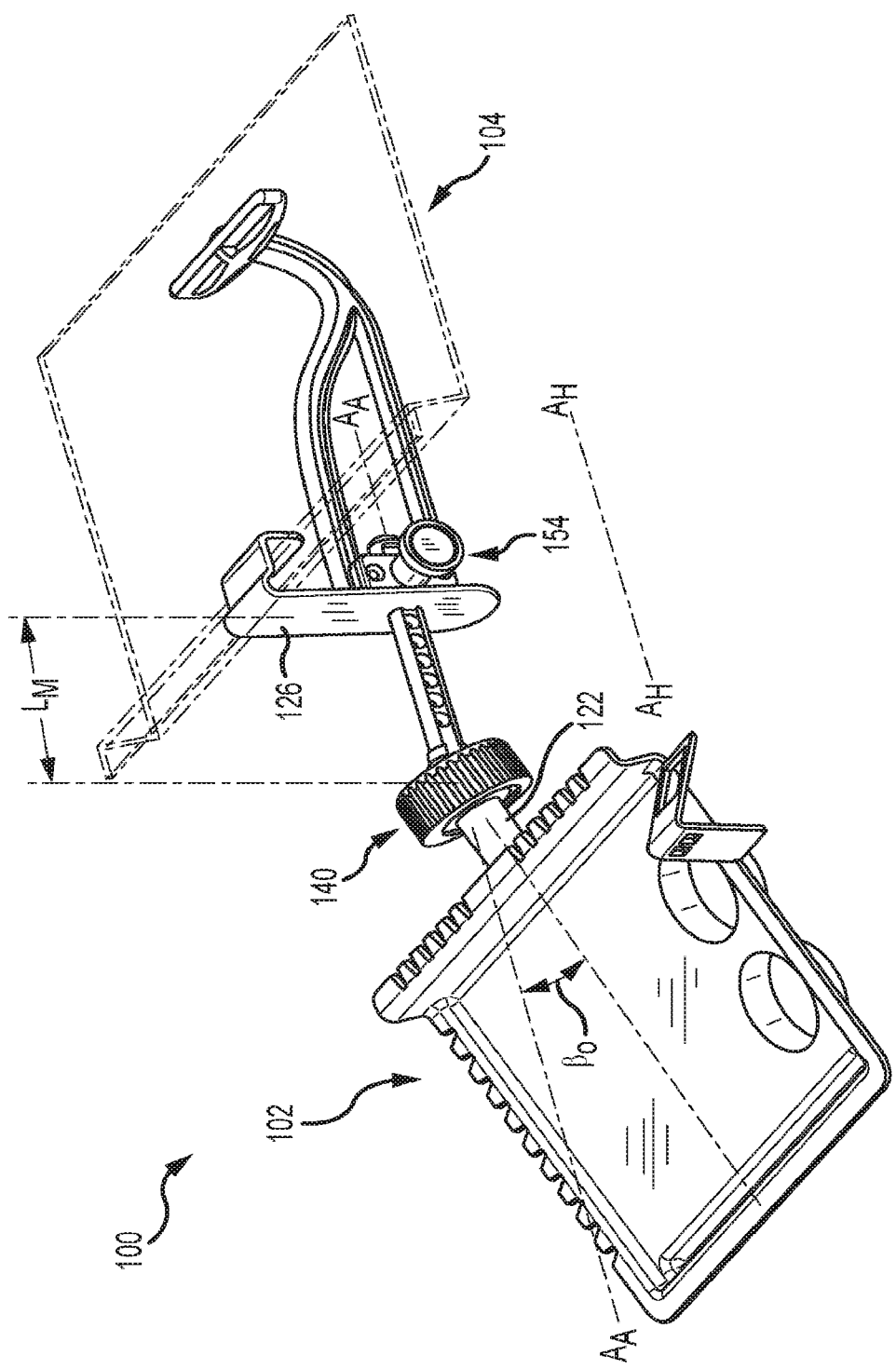

FIGS. 4A and 4B are front perspective views of the staging tray assembly 100 of FIG. 1, depicting extreme linear and angular positions of the staging tray 102, relative to the bracket 104. FIG. 4A depicts the staging tray 102 in a maximum upward angular position, as well as a linear position proximate to the interface 126 of the bracket 104. FIG. 4B depicts the staging tray 102 in a maximum downward angular position, as well as a linear position distal to the interface 126 of the bracket 104. A horizontal axis $A_H$ (generally substantially parallel to an operating suite floor, substantially orthogonal to the force of gravity) is depicted for reference. Although FIG. 4A depicts the staging tray 102 positioned in the maximum upward angular position, as well as in the linear position closest to the interface 126, it will be apparent that the staging tray 102 could also be positioned in the maximum upward angular position, while being in the linear position farthest from the interface 126 (or at any location between the farthest and closest linear positions). FIGS. 4A and 4B simply depict maximum angular and linear positions of the staging tray 102 relative to the bracket 104. These maximum and minimum angular and linear positions are not mutually exclusive to the depicted positions.

The armature 136 defines an armature axis $A_A$. In certain embodiments, the maximum upward angular position $\beta_U$ of the staging tray 102, and as measured from the armature axis $A_A$, may be up to about 60 degrees. In another embodiment, the maximum upward angular position $\beta_U$ of the staging tray 102 may be up to about 45 degrees. Maximum upward angular positions $\beta_U$ of the staging tray 102 of up to about 30 degrees and about 15 degrees are also contemplated. In certain embodiments, the maximum downward angular position $\beta_D$ of the staging tray 102, and as measured from the armature axis $A_A$, may be up to about 60 degrees. In another embodiment, the maximum downward angular position $\beta_D$ of the staging tray 102 may be up to about 45 degrees. Maximum downward angular positions $\beta_D$ of the staging tray 102 of up to about 30 degrees and about 15 degrees are also contemplated. When using a ball and socket joint 140 having an unlimited range of motion, sideways angular positions may be of similar maximum angles. A maximum linear distance $L_M$ between the ball and socket joint 140 and the interface 126 is generally limited by the length of the armature 136, and in certain embodiments may be up to about 6 inches, up to about 4 inches, or up to about 2 inches.

Figure 5A:
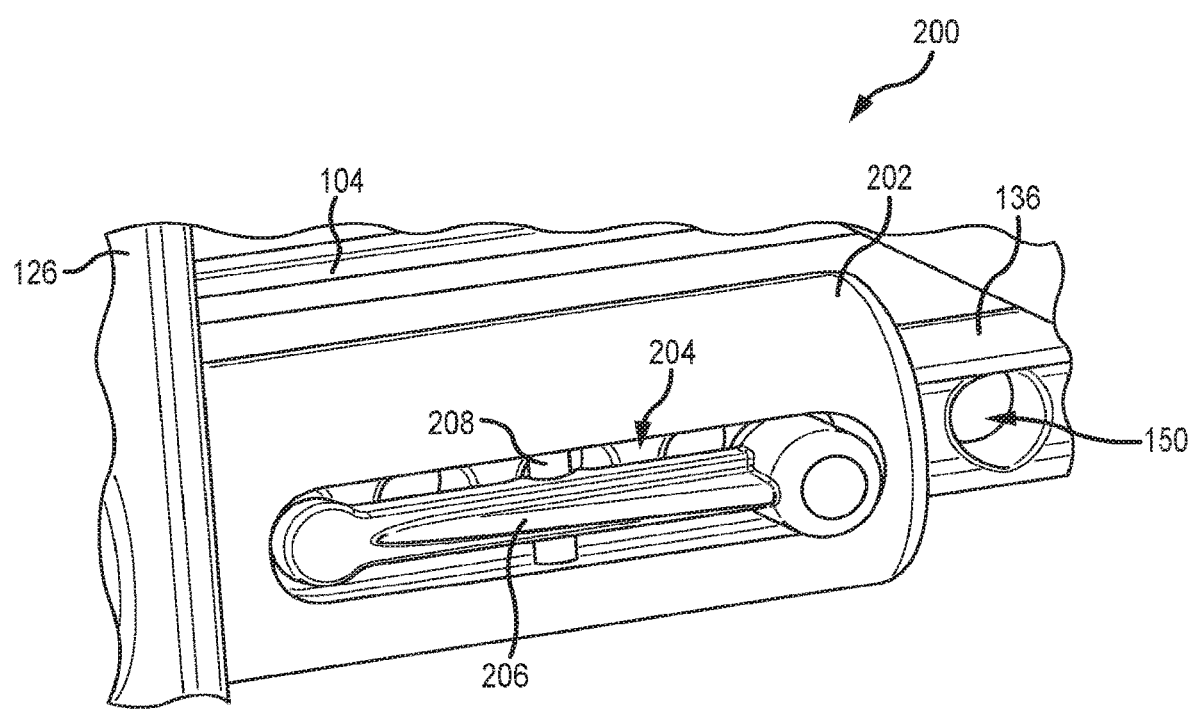
FIG. 5A is a partial enlarged perspective view of a linear locking element in accordance with an embodiment of the present technology.
Figure 5B:
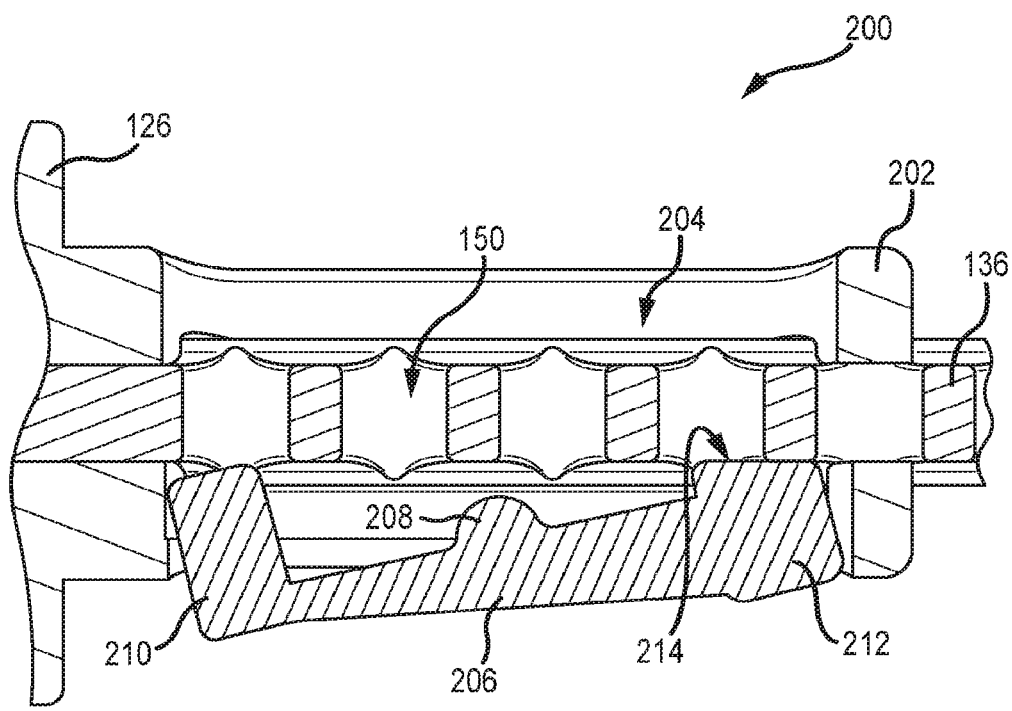
FIG. 5B is a top sectional view of the linear locking element of FIG. 5A.

Angular and linear position adjustment systems other than those depicted in the above figures can be utilized to adjust and set the positions of a staging tray relative to a medical tray. FIG. 5A is a partial enlarged perspective view of a linear locking element 200 in accordance with such an embodiment. FIG. 5B is a top sectional view of the linear locking element 200 of FIG. 5A and is described simultaneously therewith. Here, a housing 202 is secured to a rear of an interface 126 that forms a part of a bracket 104. The housing 202 defines an inner bore 204 that is sized to receive an armature 136. Each of the bracket 104, interface 126, and armature 136 are described generally above. The armature 136 defines a plurality of openings 150. A rocker 206 is pivotably connected to the housing 202 via a pin 208. The rocker 206 includes a locking end 210 and a release end 212. The locking end 210 is configured to project into one of the openings 150 when pressed inward by a user, so as to selectively lock the armature 136 in place as desired. When the user desires to adjust a linear position of the armature 136, the user presses the release end 212 of the rocker 206. This pivots the rocker 206 and disengages the locking end 210 from the opening 150. Such a disengaged position is depicted in FIG. 5B. Thereafter, the armature 136 can be moved and the locking end 210 again pressed so as to lock the armature 136 in position. A face 214 of the release end 212 may be configured such that when depressed, it is not able to project into any of the openings 150. A torsion or leaf spring may be utilized to bias the locking end 210 towards the armature 136 to ensure positive locking engagement.

Figure 6:
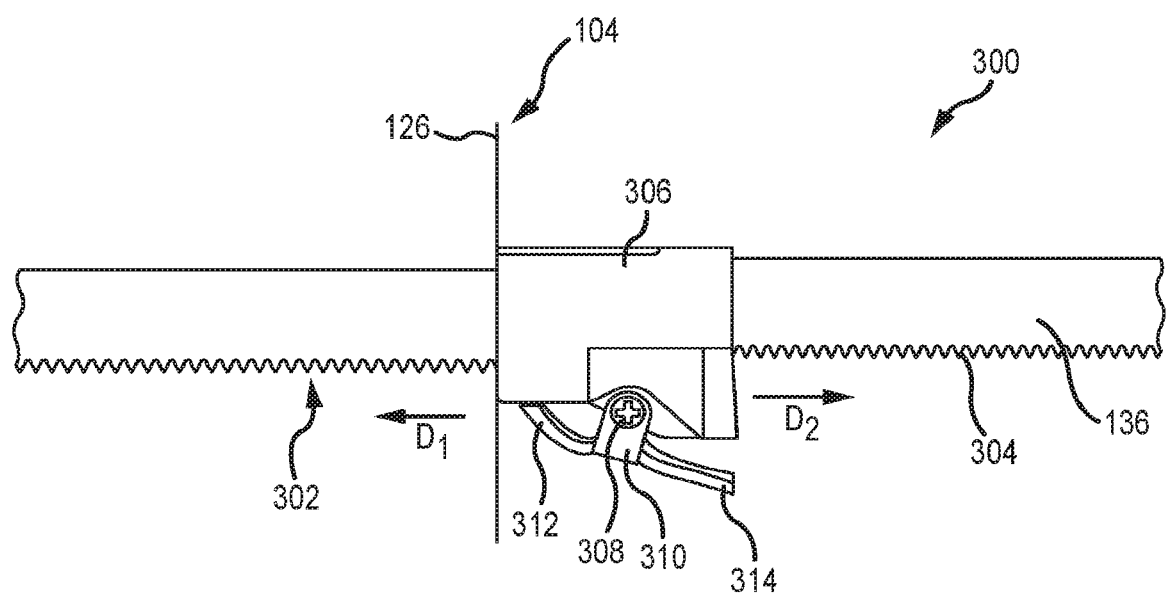
FIG. 6 is a partial side view of a linear locking element in accordance with another embodiment of the present technology.

FIG. 6 is a partial side view of a linear locking element 300 in accordance with another embodiment of the present technology. In this embodiment, the armature 136 includes a rack 302 formed by a plurality of teeth 304. A housing 306 is secured to a rear of an interface 126 that forms a part of a bracket 104. The housing 306 defines a slot (not shown) for slidably receiving the armature 136. A rocker 308 is pivotably secured to the housing 306 with a pin 310. The rocker 308 includes a locking end 312 and a release end 314. A torsion or leaf spring may be utilized to bias the locking end 312 towards the armature 136 to ensure positive locking engagement. When engaged, the locking end 312 is disposed within a gap between adjacent teeth 304, thus holding the armature 136 in place. In certain embodiments, the teeth 304 or locking end 312 may be angled such that moving the armature 136 in a first direction $D_1$, allows the rocker 308 to pivot, so as to enable adjustment of the armature 136 position without having to press the release end 314. The teeth 304 may be more steeply angled on an opposite face, such that a movement in a second direction $D_2$ will not allow pivoting of the rocker 308, thus necessitating actuation of the release end 314 so as to adjust the armature 136.

Other types of angular and linear position adjustment systems can be utilized to secure the position of the staging tray linearly and/or pivotably. For example, telescoping tubes having a rotatable locking clamp may be used to lock the linear position of the armature. Pivoting systems that utilize a plate having a number of positions defined by holes in the plate to engage with a pin can also be used.

The materials utilized in the manufacture of the staging tray assembly and the various components thereof may be those typically utilized for other equipment utilized in surgical suites. For staging tray assemblies that may be reutilized, metals such as steel, aluminum, or stainless steel can be used. Additionally, robust reinforced plastics can also be used. Such materials utilized in reusable assemblies should be able to withstand temperatures generated in an autoclave. Disposable plastics can also be utilized. It may be desirable, however that these materials could also be sterilized prior to use.

This disclosure described some embodiments of the present technology with reference to the accompanying drawings, in which only some of the possible embodiments were shown. Other aspects can, however, be embodied in many different forms and should not be construed as limited to the embodiments set forth herein. Rather, these embodiments were provided so that this disclosure was thorough and complete and fully conveyed the scope of the possible embodiments to those skilled in the art.

Although specific embodiments were described herein, the scope of the technology is not limited to those specific embodiments. One skilled in the art will recognize other embodiments or improvements that are within the scope of the present technology. Therefore, the specific structure, acts, or media are disclosed only as illustrative embodiments. The scope of the technology is defined by the following claims and any equivalents therein.

What is claimed is:

1. An apparatus comprising:
 a staging tray;
 a bracket comprising a hooked upper arm, an interface having a top portion and a bottom portion, and a lower arm terminating in a bumper, wherein the hooked upper arm extends from the interface proximate the top portion, wherein the lower arm extends from the interface proximate the bottom portion, wherein the hooked upper arm is engageable with an upper lip of a medical tray, and wherein the bumper is affixed substantially perpendicular to the lower arm such that the bumper is longitudinally engageable with a bottom surface of the medical tray; and a connection mechanism for connecting the bracket to the staging tray, wherein the connection mechanism is configured to position the staging tray both angularly and linearly relative to the bracket, and wherein at least a portion of the connection mechanism is slidable through the interface to selectively position the staging arm linearly relative to the bracket.

2. The apparatus of claim 1, wherein the staging tray at least partially defines at least one of a trough and a receiver.

3. The apparatus of claim 1, wherein the staging tray comprises a raised edge, wherein at least a portion of the raised edge defines at least one of a plurality of slots, a plurality of teeth, and a plurality of crenellations.

4. The apparatus of claim 1, wherein the staging tray further comprises a forceps receiver.

5. The apparatus of claim 4, wherein the forceps receiver comprises a receipt angle.

6. The apparatus of claim 1, wherein the connection mechanism comprises a ball and socket joint.

7. The apparatus of claim 6, wherein the socket is fixedly connected to the staging tray.

8. The apparatus of claim 7, wherein the connection mechanism comprises a locking element for selectively positioning the connection mechanism into a plurality of positions.

9. An apparatus comprising:
a bracket comprising a hooked upper arm, an interface having a top portion and a bottom portion, and a lower arm terminating in a bumper, wherein the hooked upper arm extends from the interface proximate the top portion and the lower arm extends from the interface proximate the bottom portion, wherein the hooked upper arm is engageable with an upper lip of a medical tray, and wherein the bumper is affixed substantially perpendicular to the lower arm such that the bumper is longitudinally engageable with a bottom surface of the medical tray; and
a staging tray movably engaged with the bracket by a connection mechanism, wherein the connection mechanism is configured to position the staging tray both angularly and linearly relative to the bracket, and wherein at least a portion of the connection mechanism is slidable through the interface to selectively position the staging tray linearly relative to the bracket.

10. The apparatus of claim 9, further comprising:
an angular adjustment system comprising:
a ball and socket joint engaged with at least one of the bracket and the staging tray; and
a rotatable lock for engaging at least one of the ball and the socket so as to selectively angularly position the staging tray relative to the bracket.

11. The apparatus of claim 10, further comprising:
a linear adjustment system comprising:
an armature having the plurality of openings, wherein the armature slidably engages with at least one of the bracket and the staging tray; and
a locking element for engaging the plurality of openings of the armature so as to selectively linearly position the staging tray relative to the bracket.

12. The apparatus of claim 11, wherein at least one of the ball and the socket is fixed to the armature.

13. The apparatus of claim 11, wherein the locking element comprises at least one of a fixed pin, a retractable pin, a spring-loaded pin, and a clamp.

14. The apparatus of claim 10, wherein the ball and socket joint is configured for movement along a single plane.

15. The apparatus of claim 10, wherein the ball and socket joint is positionable in a first extreme position and a second extreme position approximately 90 degrees from the first extreme position.

16. An apparatus comprising:
a staging tray comprising:
a staging surface, wherein the staging surface defines at least one receiver and at least partially defines a trough; and
a raised perimeter substantially surrounding the staging surface, wherein at least a portion of the raised perimeter at least partially defines at least one cut-out;
a bracket comprising a hooked upper arm, an interface having a top portion and a bottom portion, and a lower arm terminating in a bumper, wherein the hooked upper arm extends from the interface proximate the top portion and the lower arm extends from the interface proximate the bottom portion, wherein the hooked upper arm is engageable with an upper lip of a medical tray, and wherein the bumper is affixed substantially perpendicular to the lower arm such that the bumper is longitudinally engageable with a bottom surface of the medical tray; and
a connection mechanism configured to position the staging tray both angularly and linearly relative to the bracket, and wherein at least a portion of the connection mechanism is slidable through the interface to selectively position the staging arm linearly relative to the bracket.

* * * * *